(12) United States Patent
Desai et al.

(10) Patent No.: US 8,067,063 B2
(45) Date of Patent: Nov. 29, 2011

(54) STRETCH COMPOSITES AND METHODS OF MAKING THE COMPOSITE

(75) Inventors: Fred Naval Desai, Fairfield, OH (US); Urmish Popatlal Dalal, Milford, OH (US); Mark William Hamersky, Hamilton, OH (US); Steven Daryl Smith, Fairfield, OH (US)

(73) Assignee: The Procter & Gamble Copany, Cincinnati, OH (US)

( * ) Notice: Subject to any disclaimer, the term of this patent is extended or adjusted under 35 U.S.C. 154(b) by 68 days.

(21) Appl. No.: 12/630,118

(22) Filed: Dec. 3, 2009

(65) Prior Publication Data

US 2010/0116418 A1    May 13, 2010

Related U.S. Application Data

(63) Continuation of application No. 10/288,126, filed on Nov. 5, 2002.

(60) Provisional application No. 60/337,804, filed on Nov. 5, 2001, provisional application No. 60/400,282, filed on Jul. 31, 2002.

(51) Int. Cl.
*B05D 5/00* (2006.01)
*A41B 9/00* (2006.01)

(52) U.S. Cl. ............................. 427/256; 2/400

(58) Field of Classification Search .................. 427/256; 2/400
See application file for complete search history.

(56) References Cited

U.S. PATENT DOCUMENTS

| | | |
|---|---|---|
| 2,413,970 A | 1/1947 | Hawley, Jr. |
| 3,687,754 A | 8/1972 | Stumpf |
| 3,708,361 A | 1/1973 | Stumpf |
| 3,816,228 A | 6/1974 | Stumpf |
| 3,981,838 A | 9/1976 | Wilson |
| 4,223,059 A * | 9/1980 | Schwarz ..................... 428/198 |
| 4,322,467 A | 3/1982 | Heimbach et al. |
| 4,618,384 A | 10/1986 | Sabee |
| 4,618,630 A | 10/1986 | Knobel et al. |
| 4,705,584 A | 11/1987 | Lauchenauer |
| 4,834,741 A | 5/1989 | Sabee |
| 4,968,313 A | 11/1990 | Sabee |
| 5,055,103 A | 10/1991 | Nomura et al. |
| 5,085,655 A | 2/1992 | Mann et al. |
| 5,151,092 A | 9/1992 | Buell et al. |
| 5,156,793 A | 10/1992 | Buell et al. |
| 5,217,798 A | 6/1993 | Brady et al. |
| 5,221,274 A | 6/1993 | Buell et al. |
| 5,232,777 A | 8/1993 | Sipinen et al. |

(Continued)

FOREIGN PATENT DOCUMENTS

EP    0 472 942 B1    9/1995

(Continued)

*Primary Examiner* — Timothy Meeks
*Assistant Examiner* — Mandy Louie
(74) *Attorney, Agent, or Firm* — Andrew A Paul; John P. Colbert

(57) ABSTRACT

A stretch composite having one or more elastomeric members disposed on at least one region of an extensible fibrous substrate to provide stretch properties to a targeted region of the substrate. The composite has been incrementally stretched to at least partially break up the structure of the substrate in order to reduce its resistance to stretch. The stretch composites are useful for disposable and durable articles, such as disposable absorbent articles including diapers, pull-on diapers, training pants, incontinence briefs, catamenial garments, baby bibs, and the like, and durable articles like garments including sportswear, outerwear and the like. The present invention also relates to methods of forming such stretch composites.

12 Claims, 8 Drawing Sheets

U.S. PATENT DOCUMENTS

| | | | |
|---|---|---|---|
| 5,234,423 | A | 8/1993 | Alemany et al. |
| 5,330,458 | A | 7/1994 | Buell et al. |
| 5,342,291 | A | 8/1994 | Scholz et al. |
| 5,356,683 | A | 10/1994 | Egolf et al. |
| 5,431,644 | A | 7/1995 | Sipinen et al. |
| 5,440,764 | A | 8/1995 | Matsushita |
| 5,487,780 | A | 1/1996 | Ritter |
| H1517 | H | 2/1996 | Erickson et al. |
| 5,499,978 | A | 3/1996 | Buell et al. |
| 5,503,076 | A | 4/1996 | Yeo |
| 5,527,304 | A | 6/1996 | Buell et al. |
| 5,591,152 | A | 1/1997 | Buell et al. |
| 5,628,741 | A | 5/1997 | Buell et al. |
| 5,653,704 | A | 8/1997 | Buell et al. |
| 5,662,758 | A | 9/1997 | Hamilton et al. |
| 5,671,678 | A | 9/1997 | Bolte et al. |
| 5,674,216 | A | 10/1997 | Buell et al. |
| 5,681,302 | A | 10/1997 | Melbye et al. |
| 5,690,627 | A | 11/1997 | Clear et al. |
| RE35,687 | E | 12/1997 | Igaue et al. |
| 5,711,832 | A * | 1/1998 | Glaug et al. ............ 156/73.1 |
| 5,749,865 | A | 5/1998 | Yamamoto et al. |
| 5,843,057 | A | 12/1998 | McCormack |
| 5,853,859 | A | 12/1998 | Levy et al. |
| 5,863,330 | A | 1/1999 | Le riche et al. |
| 5,871,607 | A | 2/1999 | Hamilton et al. |
| 5,885,722 | A | 3/1999 | Ritter |
| 5,910,224 | A | 6/1999 | Morman |
| 5,914,084 | A | 6/1999 | Benson et al. |
| 5,964,973 | A | 10/1999 | Heath et al. |
| 6,030,372 | A | 2/2000 | Buell et al. |
| 6,069,097 | A | 5/2000 | Suzuki et al. |
| 6,139,675 | A | 10/2000 | Druecke et al. |
| 6,193,701 | B1 | 2/2001 | Van gompel et al. |
| 6,193,918 | B1 | 2/2001 | McGuire et al. |
| 6,245,050 | B1 | 6/2001 | Odorzynski et al. |
| 6,313,372 | B1 | 11/2001 | Suzuki |
| 6,323,389 | B1 | 11/2001 | Thomas et al. |
| 6,465,073 | B1 | 10/2002 | Morman et al. |
| 6,476,289 | B1 | 11/2002 | Buell et al. |
| 6,495,229 | B1 | 12/2002 | Carte et al. |
| 6,531,025 | B1 | 3/2003 | Lender et al. |
| 6,531,027 | B1 | 3/2003 | Lender et al. |
| 6,682,514 | B1 | 1/2004 | Brunner |
| 6,706,649 | B2 | 3/2004 | Schwinn |
| 6,827,806 | B2 | 12/2004 | Uitenbroek et al. |
| 6,833,179 | B2 | 12/2004 | May et al. |
| 6,875,710 | B2 | 4/2005 | Eaton et al. |
| 6,939,334 | B2 | 9/2005 | Odorzynski et al. |
| 7,056,411 | B2 * | 6/2006 | Desai et al. ............ 156/277 |
| 7,163,740 | B2 | 1/2007 | Rosati |
| 2002/0007164 | A1 | 1/2002 | Boggs et al. |
| 2002/0009940 | A1 | 1/2002 | May et al. |
| 2002/0089888 | A1 | 7/2002 | Kato |
| 2002/0115817 | A1 | 8/2002 | Hayes |
| 2002/0180097 | A1 | 12/2002 | Giachetto et al. |
| 2003/0084996 | A1 | 5/2003 | Alberg et al. |
| 2003/0087059 | A1 | 5/2003 | Jackson et al. |
| 2003/0087098 | A1 | 5/2003 | Eaton et al. |
| 2003/0088220 | A1 | 5/2003 | Molander et al. |
| 2003/0088228 | A1 | 5/2003 | Desai et al. |
| 2003/0091807 | A1 | 5/2003 | Desai et al. |
| 2004/0024109 | A1 * | 2/2004 | Hamersky et al. ............ 524/505 |
| 2004/0044323 | A1 | 3/2004 | Roessler et al. |
| 2004/0127881 | A1 | 7/2004 | Stevens et al. |
| 2004/0134596 | A1 | 7/2004 | Rosati et al. |
| 2004/0142110 | A1 | 7/2004 | Branca et al. |
| 2004/0222553 | A1 | 11/2004 | Desai et al. |
| 2005/0215973 | A1 | 9/2005 | Roe et al. |
| 2006/0212017 | A1 | 9/2006 | Desai et al. |
| 2006/0271006 | A1 | 11/2006 | Desai et al. |
| 2006/0271007 | A1 | 11/2006 | Desai et al. |
| 2007/0029035 | A1 | 2/2007 | Desai et al. |

FOREIGN PATENT DOCUMENTS

| | | |
|---|---|---|
| EP | 0 745 433 B1 | 12/1996 |
| EP | 1 081 672 A2 | 3/2001 |
| JP | 10-053963 | 2/1998 |
| WO | WO 92/15446 | 9/1992 |
| WO | WO 94/01507 A1 | 1/1994 |
| WO | WO 96/24485 A1 | 8/1996 |
| WO | WO 96/38114 A1 | 12/1996 |
| WO | WO 99/48680 | 9/1999 |
| WO | WO 00/07532 A1 | 2/2000 |
| WO | WO 00/07533 A1 | 2/2000 |
| WO | WO 01/00053 A1 | 1/2001 |
| WO | WO 01/00915 A1 | 1/2001 |
| WO | WO 01/15645 A1 | 3/2001 |
| WO | WO 01/87212 A1 | 11/2001 |
| WO | WO 01/87213 A1 | 11/2001 |
| WO | WO 01/87214 A1 | 11/2001 |
| WO | WO 01/87588 A2 | 11/2001 |
| WO | WO 02/053003 A2 | 7/2002 |
| WO | WO 02/098999 | 12/2002 |
| WO | WO 02/098999 A2 | 12/2002 |
| WO | WO 03/039420 A2 | 5/2003 |
| WO | WO 03/039421 A2 | 5/2003 |
| WO | WO 03/039426 A2 | 5/2003 |
| WO | WO 03/039834 A1 | 5/2003 |
| WO | WO 03/039853 A1 | 5/2003 |
| WO | WO 03/039868 A1 | 5/2003 |

* cited by examiner

STRETCH COMPOSITES AND METHODS OF MAKING THE COMPOSITE

CROSS REFERENCE TO RELATED APPLICATION

This patent application is a continuation of U.S. application Ser. No. 10/288,126, filed Nov. 5, 2002; which claims the benefit of U.S. Provisional Application No. 60/337,804, filed Nov. 5, 2001; and U.S. Provisional Application No. 60/400,282, filed Jul. 31, 2002.

FIELD OF THE INVENTION

A stretch composite having one or more elastomeric members disposed on at least one region of an extensible fibrous substrate to provide stretch properties to a targeted region of the substrate. The composite has been incrementally stretched to at least partially break up the structure of the substrate in order to reduce its resistance to stretch. The stretch composites are useful for disposable and durable articles, such as disposable absorbent articles including diapers, pull-on diapers, training pants, incontinence briefs, catamenial garments, baby bibs, and the like, and durable articles like garments including sportswear, outerwear and the like. The present invention also relates to methods of forming such stretch composites.

BACKGROUND

Disposable absorbent products, such as diapers, training pants, incontinence articles typically include stretchable materials, such as elastic strands, in the waist region and the cuff regions to provide a snug fit and a good seal of the article. Pant-type absorbent articles further include stretchable materials in the side portions for easy application and removal of the article and for sustained fit of the article. Stretchable materials have also been used in the ear portions for adjustable fit of the article.

There are various approaches to provide desirable elastic properties in those areas. Stretchable materials may be films or nonwoven fibrous webs made of elastomeric materials. Typically, such materials are stretchable in any direction. However, because the films or webs are made entirely of elastomeric materials, they are relatively expensive, and they tend to have more drag on skin surface, resulting in discomforts to the wearer of the article. Sometimes, the stretchable films are laminated to one or more layers of nonwoven webs. Since typical nonwoven webs typically are made of thermoplastic fibers, they have very limited stretchability and, the resulting laminates provide considerable resistance to stretch. It is necessary to reduce this resistance substantially in order to make functional stretch laminates.

Other approaches to make stretchable materials are also known, including: stretch-bonded laminates (SBL) and necked-bonded laminates (NBL). Stretch bonded laminates are made by stretching the elastic strands in the machine direction (MD), laminating it to one or more nonwoven substrates while it is in the stretched state, and releasing the tension in the elastic strands so that the nonwovens gather and take on a puckered shape. Necked-bonded laminates are made by first stretching the nonwoven substrate in the machine direction such that it necks (i.e., reduces its dimension) at least in the cross machine direction (CD), then bonding the elastic strands to the substrate while the substrate is still in the stretched, necked state. This laminate will be stretchable in CD, at least up to the original width of the nonwoven before it was necked. Combinations of stretch bondings and neck bondings have also been known to deliver stretch in both MD and CD direction. In these approaches, at least one of the components is in a tensioned (i.e., stretched) state when the components of the laminates are joined wherein.

Zero strain stretch laminates are also known. The zero strain stretch laminates are made by bonding the elastomer to the nonwoven while both are in an unstrained state. The laminates are then incrementally stretched to impart the stretch properties. The incrementally stretched laminates are stretchable only to the extent afforded by the non-recovered (i.e., residual) extensibility of the laminate. For example, U.S. Pat. No. 5,156,793, issued to Buell et al., discloses a method for incrementally stretching the elastomeric-nonwoven laminate web, in a non-uniform manner, to impart elasticity to the resulting laminate.

In all the approaches above, stretch laminates are made separately. The stretch laminates must be cut into the appropriate size and shape, then adhesively attached to the desired location in the product in a process sometimes referred as the "cut-and-slip" process. Because of the different stretch properties required for different elements of the product, it is necessary to make a variety of laminates having different stretchability and cut the laminates to different sizes and shapes. Several cut and slip units may be needed to handle the different stretchability of the stretch laminates and to attach them to different locations of the product. As the number of cut-and-slip units and/or steps multiplies, the process quickly becomes cumbersome and complicated.

Based on the foregoing, it is desirable to have a cost effective stretch composite having elastomeric materials disposed only in specific areas in specific amount for stretchability to provide desired in-use benefits of an article, such as sealing, gasketing, containing, body-conforming, or fit. It is also desirable to have a stretch composite delivering stretchability in targeted areas among discrete, spaced apart components of the article. It is further desirable to have stretch composites delivering targeted stretchability locally (i.e., within a component of the article).

Moreover, it is desirable to have an efficient and cost effective process that does not involve multi-steps and/or multi-units and that delivers stretch properties to various portions of the absorbent article. Such process for making the above stretch composites is desirable because it has total flexibility that allows for controlled deposition of different types and/or amount of elastomeric materials to the targeted areas only. Such process is also desirable because it tailors the delivery of stretchability and resistance to stretch in various portions of a product to deliver improved fit and comfort to the wearer.

SUMMARY OF THE INVENTION

The present invention relates to a stretch composite comprising an extensible fibrous substrate having at least one elastomeric member disposed on at least a portion of the substrate to form an elasticized region, wherein the elastomeric member has an average width greater than about 0.2 mm, a melt viscosity of from about 1 to about 150 Pa·s, measured at 175° C. and 1 s$^{-1}$; an elasticity at least about 50 N/m; and a percent set of less than about 20%.

The stretch composite may be used for portions of an absorbent article to provide desired benefits including better fit, improved comfort, lower forces to put on and/or take off the article. The portions of the absorbent article that desire stretchability typically include, but are not limited to, the waist regions, the leg cuffs, side panels, ear portions, topsheet, outercover and the fastener system.

All documents cited are, in relevant part, incorporated herein by reference; the citation of any document is not to be construed as an admission that it is prior art with respect to the present invention.

BRIEF DESCRIPTION SHOWN IN THE DRAWINGS

While the specification concludes with claims particularly pointing out and distinctly claiming the subject matter which is regarded as the present invention, it is believed that the invention will be more fully understood from the following description taken in conjunction with the accompanying drawings, in which:

DETAILED DESCRIPTION OF THE INVENTION

Figure 1:
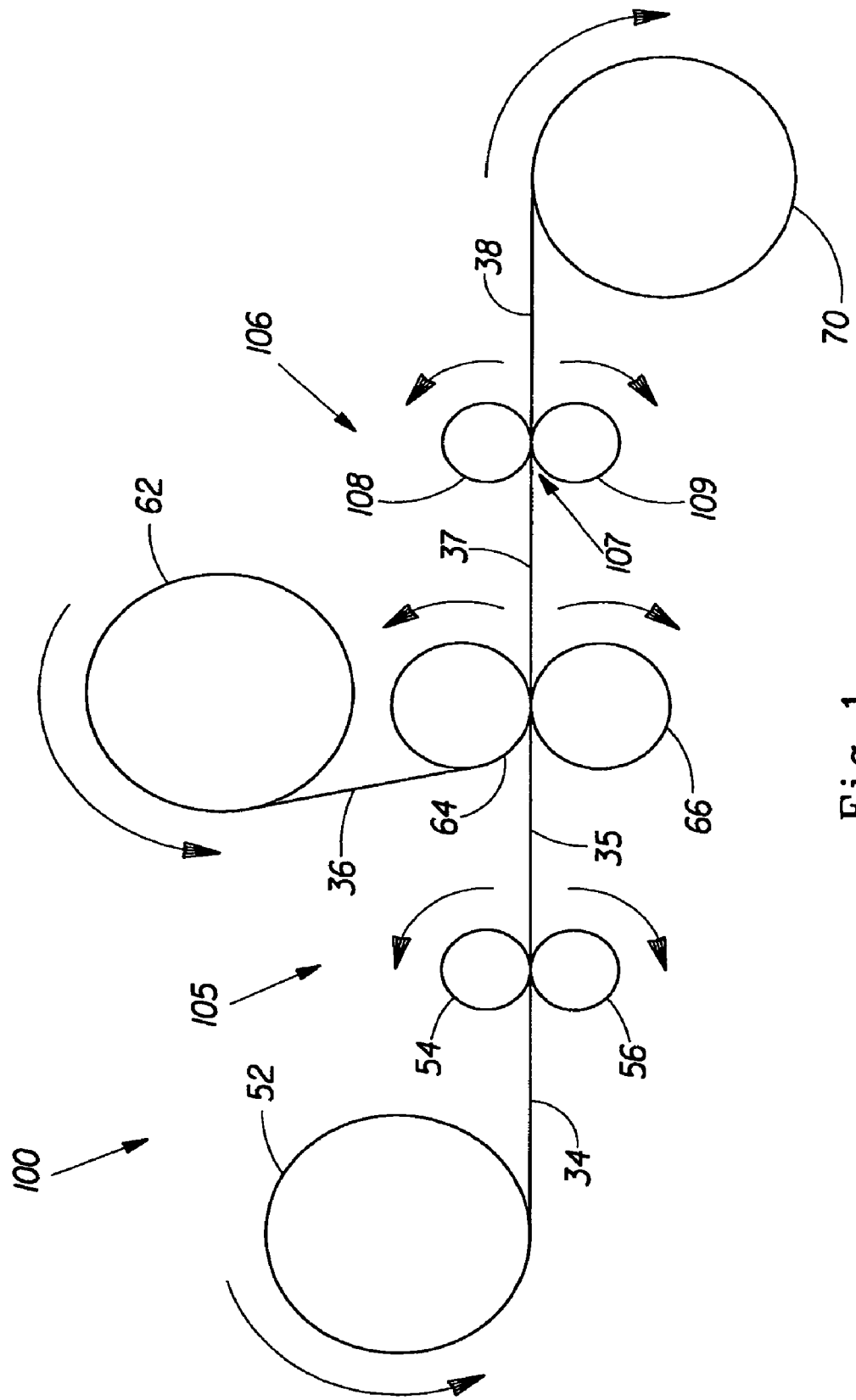
FIG. 1 is a schematic illustration of a representative process of the present invention.

The term "disposable" as used herein refers to describe products which generally are not intended to be laundered or otherwise restored or extensively reused in their original function, i.e., preferably they are intended to be discarded after about 10 uses or after about 5 uses or after about a single use. It is preferred that such disposable articles be recycled, composted or otherwise disposed of in an environmentally compatible manner.

The term "durable" as used herein refers to describe products which generally are intended to be laundered or otherwise restored or extensively reused in their original function, i.e., preferably they are intended to be used more than about 10 times.

The term "disposable absorbent article" as used herein refers to a device that normally absorbs and retains fluids. In certain instances, the phrase refers to devices that are placed against or in proximity to the body of the wearer to absorb and contain the excreta and/or exudates discharged from the body, and includes such personal care articles as fastened diapers, pull-on diapers, training pants, swim diapers, adult incontinence articles, feminine hygiene articles, and the like. In other instances, the term also refers to protective or hygiene articles, for example, bibs, wipes, bandages, wraps, wound dressings, surgical drapes, and the like.

The term "web" as used herein refers to any continuous material, including a film, a nonwoven fabric, a woven fabric, a foam or a combination thereof, or a dry lap material including wood pulp, and the like, having a single layer or multiple layers.

The term "substrate" as used herein refers to any material, including a film, a nonwoven web, a woven web, a foam or a combination thereof, or a dry lap material including wood pulp, cellulosic materials, derivatized or modified cellulosic materials, and the like, having a single layer or multiple layers.

The term "fibrous substrate" as used herein refers to a material comprised of a multiplicity of fibers that could be either a natural or synthetic material or any combination thereof. For example, nonwoven materials, woven materials, knitted materials, and any combinations thereof.

The term "nonwoven" as used herein refers to a fabric made from continuous filaments and/or discontinuous fibers, without weaving or knitting by processes such as spun-bonding, carding and melt-blowing. The nonwoven fabric can comprise one or more nonwoven layers, wherein each layer can include continuous filaments or discontinuous fibers. Nonwoven can also comprise bi-component fibers, which can have shell/core, side-by-side, or other known fiber structures.

The term "elastomer" as used herein refers to a polymer exhibiting elastic properties.

The term "elastic" or "elastomeric" as used herein refers to any material that upon application of a biasing force, can stretch to an elongated length of at least about 160 percent of its relaxed, original length, without rupture or breakage, and upon release of the applied force, recovers at least about 55% of its elongation, preferably recovers substantially to its original length that is, the recovered length being less than about 120 percent, preferably less than about 110 percent, more preferably less than about 105 percent of the relaxed original length.

The term "inelastic" refers herein to any material that does not fall within the definition of "elastic" above.

The term "extensible" or "inelastically elongatable" refers herein to any material that upon application of a biasing force to stretch beyond about 110 percent of its relaxed original length will exhibit permanent deformation, including elongation, rupture, breakage, and other defects in its structure, and/or changes in its tensile properties.

The stretch composite of the present invention comprises one or more elastomeric members disposed on and at least partially penetrating a portion of an extensible fibrous substrate, which is permanently elongated in the finished composite. Different elastomeric members can be disposed on spaced-apart, adjacent or overlapping portions of the substrate to deliver different properties, especially different elasticity. The stretch composite can be made in situ as a portion of an article by the present process to form a desired article having a stretch laminate therein. The in-situ process eliminates additional processing steps, such as cutting, shaping, and bonding. In the process of the present invention, the expensive elastomeric material is used efficiently by delivering one or more elastomeric members to the article only where they are needed and in the amount needed. Further, the resulting product made with the laminate and the process disclosed herein can provide improved product fit and comfort.

The elastomeric members can have varied shapes and profiles in any direction, which result in desired variations in physical properties of the composite material within the elastomeric members. The planar shape in the x-y direction of the elastomeric members can be any suitable geometrical shape defining the planar dimensions of the composite material, including a rectilinear outline, a curvilinear outline, a triangle, a trapezoid, a square, a parallelogram, a polygon, an ellipse, a circle, and any combination thereof. The contour profile in the z direction of the elastomeric members can be any suitable geometric shape including linear and nonlinear profiles. The variation in the dimension in the z direction and the x-y plane can be achieved by the process of the present invention. Typically, the average width of individual elastomeric member is at least about 0.2 mm, preferably at least about 1 mm, and more preferably at least about 2 mm. The average thickness of individual elastomeric member is from about 0.1 mm to about 2.5 mm, preferably from about 0.25 mm to about 2 mm, and more preferably from about 0.5 mm to about 1.5 mm. The average width and thickness of the elastomeric members can be determined by conventional optical microscopy or by scanning electron microscopy (according to ASTM B748) for more precise measurements. For some embodiments, the thickness of the elastomeric member and/or the composite can be measured under a pressure of 0.25 psi (1.7 Kpa) using a microcaliper.

The variable physical properties may include tensile strength, elastic modulus, elasticity, conductivity, breathability (i.e., vapor and/or gas permeability), liquid impermeability, and others. Further, unique interrelationships between physical properties can be formed, for example the ratio of modulus to density, tensile strength to density, and the like.

Figure 2A:
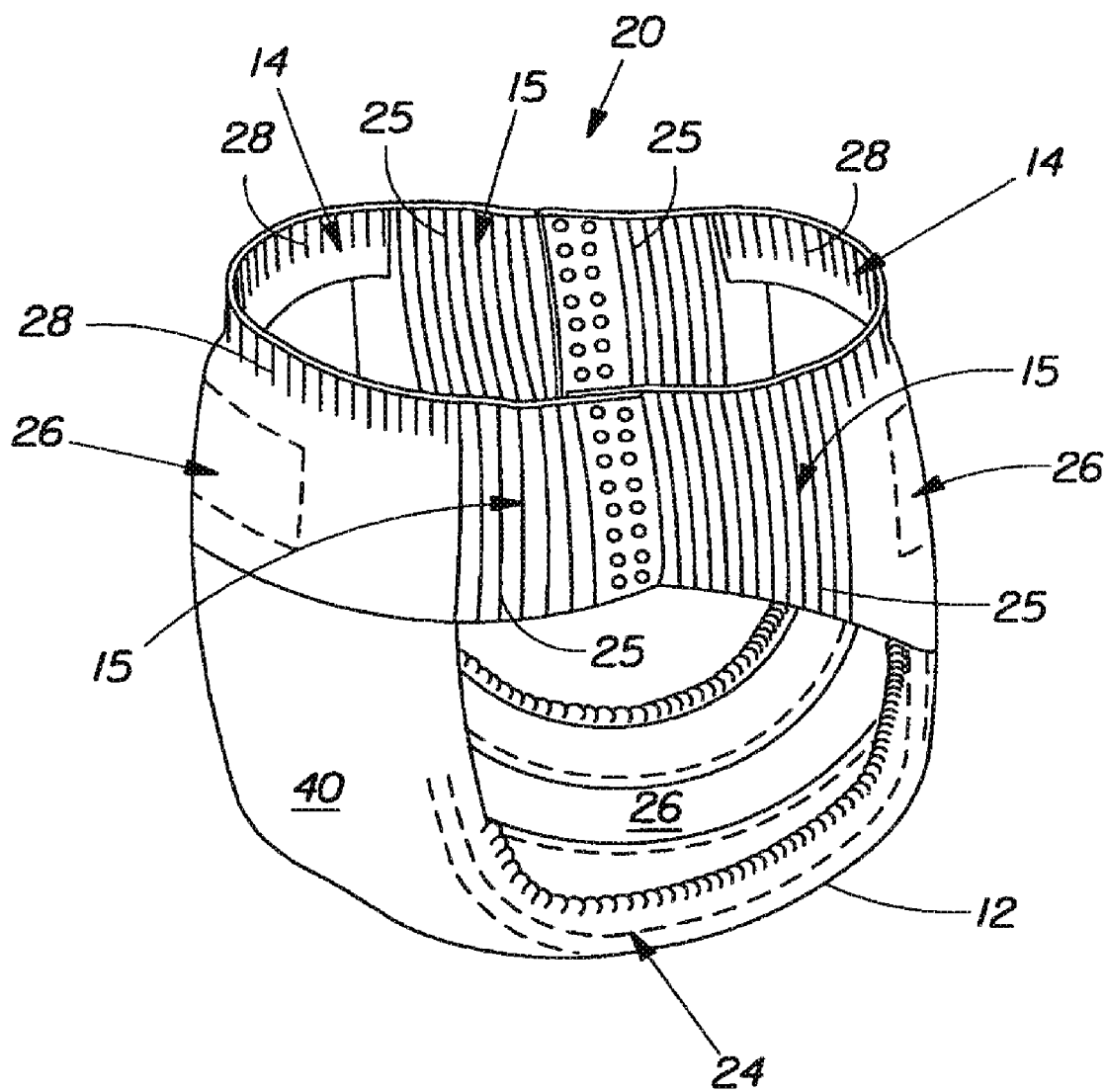
FIG. 2A is a perspective view of one embodiment of a pant type diaper containing the stretch composite of the present invention.
Figure 2B:
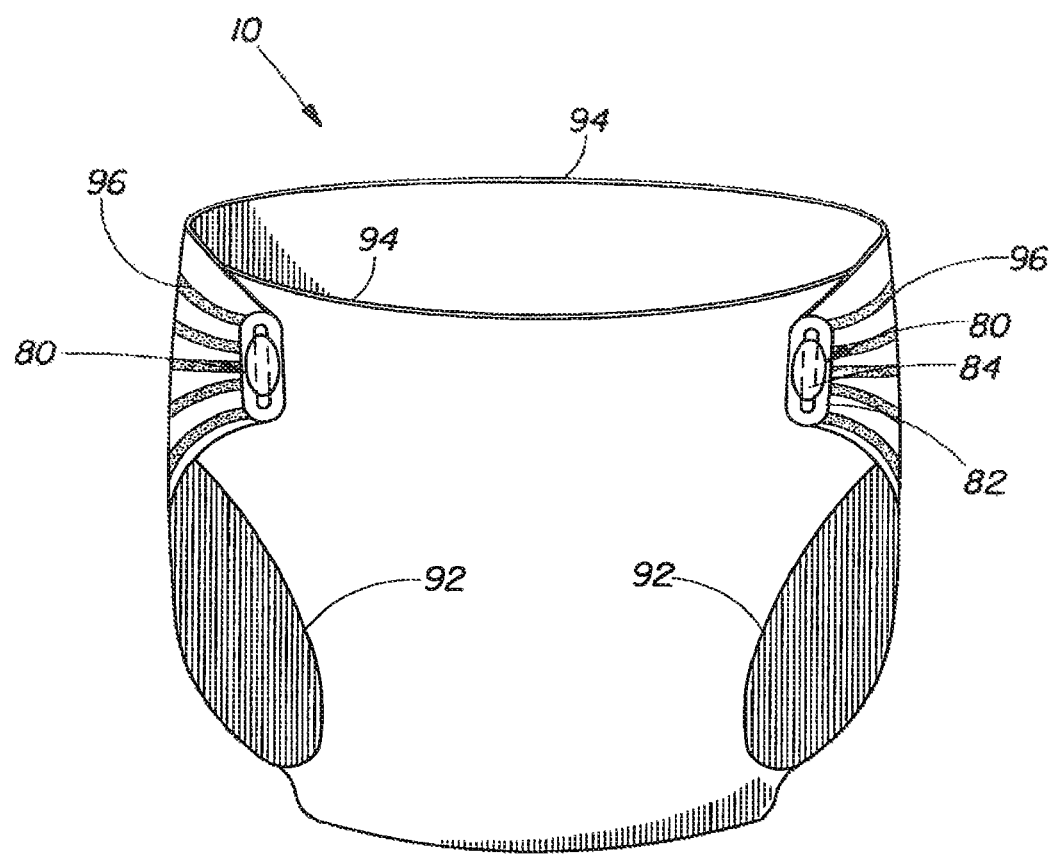
FIG. 2B is a perspective view of another embodiment of a diaper in its in-use configuration containing the stretch composite of the present invention.

FIG. 2A illustrates one embodiment of an absorbent article (a pant type diaper) in an in-use configuration, at least a portion of the article comprises the stretch laminate of the present invention. Pant type diaper 20 may comprise a plurality of elastic components on a substrate, typically a nonwoven fibrous web, to provide specific functions for the diaper. The elastic components include elasticized cuff region 12 comprising leg elastomeric members 24 for gasketing function around the legs of the wearer; elasticized waist region 14 comprising waist elastomeric members 28 for gasketing function around the waist; elasticized side panel 15 comprising panel elastomeric members 25 for adjustable fit function around the lower torso; and chassis elastomeric members 26 over outer cover 40 for adjustable fit function directed mainly to tummy, buttocks and/or the crotch areas and for adjusting the breathable (i.e., substantially vapor/gas permeable and liquid impermeable) function provided by the outer cover 40. Another embodiment, shown in FIG. 2B in an in-use configuration, is a disposable diaper 10 having elastic leg opening 92, elastic waist opening 94 and elastic ear portion 96 and the fastener system 80 comprising a slot member 82 and a tab member 84, all of which can be made of the stretch composites of the present invention. Elasticated topsheet (not shown) can also be made of the composite of the present invention.

The manufacture of these elastic components of a diaper typically include the steps of cutting from an elastomeric material (in the form of a film, a fibrous web, or a laminate) to the desired size and shape, then joining the discrete pieces of elastomeric materials to the substrate using known bonding methods such as adhesive, thermal, mechanical, ultrasonic bonding. In contrast, the present invention provides a novel process that combines the step of making of an elastomeric component and the step of joining the elastomeric component to a substrate into a single step continuous process. A given elastic component may comprise a single elastomeric member or a plurality of elastomeric members. Moreover, in the present invention, the elastomeric members can be applied directly onto multiple portions, corresponding to discrete elastic components of the diaper to form the waist elastomeric members, leg elastomeric members, etc., in one continuous process. The present invention is well suited to deliver different elasticity's to meet the different requirements of individual components of the diaper. It is also contemplated by the present invention that multiple elastomeric members having different elasticities may be applied in adjacent portions on a single element of an absorbent article. The different elasticities may be achieved by variations in melt viscosities, shapes, patterns, add-on levels, compositions, and combinations thereof.

The elastomeric members may be applied in various shapes or patterns continuously or intermittently. Typically, the elastomeric members may be applied in stripes (rectilinear or curvilinear), spirals, discrete dots and the like. The elastomeric members may also be applied in various geometric or decorative shapes or figures. The various patterns may place the elastomeric members in perpendicular, parallel and/or angled (i.e., non-parallel) positions with respect to one another, or with respect to components of the diaper, such as a waist region, leg openings, side seams. Two elastomeric members are parallel when they exhibit substantially uniform inter-member or lateral spacing. They are non-parallel when they exhibit non-uniform inter-member or lateral spacing. Thus, two curvilinear elastomeric members are non-parallel if they have different curvatures. In another example, an elastomeric member is parallel to a waist region or a leg opening when the spacing between the elastomeric member and an edge of the waist region or a leg opening is substantially uniform.

Figure 3A:
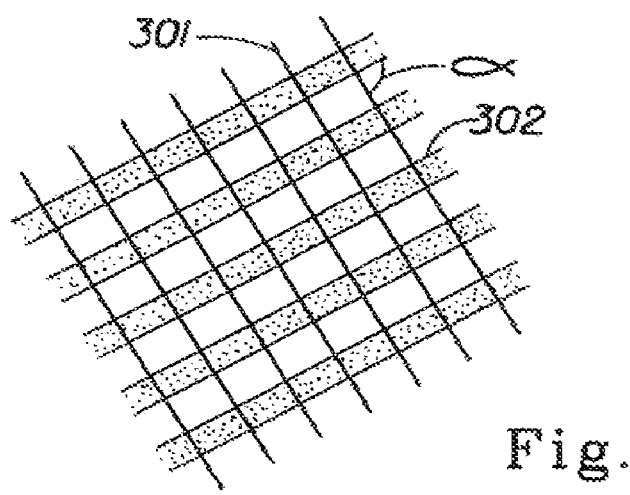
FIG. 3A is a plan view of an exemplary stretch composite with first and second elastomeric compositions applied as rectilinear stripes in parallel patterns.

In one embodiment, as shown in FIG. 3A, a plurality of rectilinear stripes of a first elastomeric composition are applied in a substantially parallel pattern along a first direction to form first elastomeric members 301. Optionally, a plurality of rectilinear stripes of a second elastomeric composition are applied in a substantially parallel pattern along a second direction to form second elastomeric members 302, the second direction being at a predetermined angle α with respect to the first direction. The predetermined angle α ranges from about zero to about 90 degrees, preferably from about 1 to about 80 degrees, and more preferably from about 5 to about 70 degrees. The first and the second elastomeric compositions can be deposited on fully or partially overlapping portions (corresponding to the same or partially overlapping elastic components of the finished diaper) of the substrate. Alternatively, the first and second elastomeric compositions can be deposited on non-overlapping (adjacent or remote) portions of the substrate, which correspond to distinct elastic components of the finished diaper. Consequently, the stripes of the first and second elastomeric compositions do not crossover.

Figure 3B:
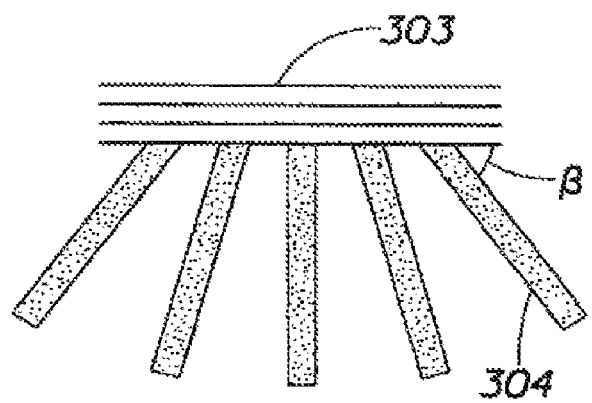
FIG. 3B is a plan view of an exemplary stretch composite with first elastomeric composition applied as rectilinear stripes in a parallel pattern and second elastomeric composition applied as rectilinear stripes in a non-parallel pattern.
Figure 3C:
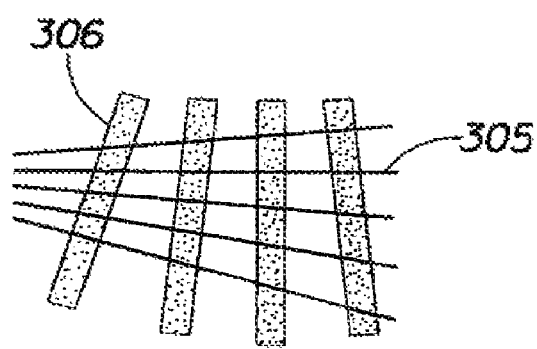
FIG. 3C is a plan view of an exemplary stretch composite with first and second elastomeric compositions applied as rectilinear stripes in non-parallel patterns.

In some embodiments, a plurality of first elastomeric members in the form of rectilinear stripes are applied in a substantially parallel pattern along a first direction, and a plurality of second elastomeric members in the form of rectilinear or curvilinear stripes are applied in a non-parallel or angled pattern, wherein at least one, preferably a plurality of the stripes of the second elastomeric members are angled or non-parallel to one or both adjacent stripes of the same elastomeric members. The first and second elastomeric members may be deposited on the same, overlapping or separate portions of the fibrous substrate. FIG. 3B illustrates one of the above embodiments wherein the first elastomeric members are substantially parallel and rectilinear stripes 303 along a first direction and the second elastomeric members are rectilinear stripes 304 which are not parallel to adjacent stripes; each stripe of the second elastomeric members forms a predetermined angle β with respect to the first direction. Specifically, the predetermined angle β ranges from about zero to about 180 degrees and varies among different stripes 304. Alternatively, the first and second elastomeric members are deposited in a non-parallel or angled pattern, and forming varying angles between the stripes 305, 306, such as the embodiment shown in FIG. 3C.

The substrate material may be films, knitted fabric, woven fibrous webs or nonwoven fibrous webs. In some embodiments, the substrates are extensible nonwoven webs made of polyolefin fibers or filaments, such as polyethylene, polypropylene.

Suitable elastomeric compositions are applied to the substrate in a fluid or fluid-like state to affect at least partial penetration into the substrate, thus, achieving sufficient bonding between the resulting elastomeric members and the substrate such that the composite exhibits insubstantially delaminate in the subsequent incremental stretching step. The elastomeric composition may have a melt viscosity from about 1 to about 150 Pa·s, preferably from about 5 to about 100 Pa·s, and more preferably from about 10 to about 80 Pa·s, at 175° C. and 1 s$^{-1}$ shear rate. Such elastomeric composition is suitable for use in the present processes that operate at a lower viscosity and/or lower temperature than the processing conditions of a typical melt extrusion and/or fiber spinning process.

Suitable elastomeric compositions comprise thermoplastic elastomers selected from the group consisting of styrenic block copolymers, metallocene-catalyzed polyolefins, polyesters, polyurethanes, polyether amides, and combinations thereof. Suitable styrenic block copolymers may be diblock, triblock, tetrablock, or other multi-block copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON® from the Shell Chemical Company of Houston, Tex.; SEPTON® from Kuraray America, Inc. of New York, N.Y.; and VECTOR® from Dexco Chemical Company of Houston, Tex. Commercially available metallocene-catalyzed polyolefins include EXXPOL® and EXACT® from Exxon Chemical Company of Baytown, Tex.; AFFINITY® and ENGAGE® from Dow Chemical Company of Midland, Mich. Commercially available polyurethanes include ESTANE® from Noveon, Inc., Cleveland, Ohio. Commercial available polyether amides include PEBAX® from Atofina Chemicals of Philadelphia, Pa. Commercially available polyesters include HYTREL® from E. I. DuPont de Nemours Co., of Wilmington, Del.

The elastomeric compositions may further comprise processing aids and/or processing oils to adjust the melt viscosity of the compositions to the desired range. They include the conventional processing oil, such as mineral oil, as well as other petroleum-derived oils and waxes, such as parafinic oil, naphthenic oil, petrolatum, microcrystalline wax, paraffin or isoparaffin wax. Synthetic waxes, such as Fischer-Tropsch wax; natural waxes, such as spermaceti, carnauba, ozokerite, beeswax, candelilla, paraffin, ceresin, esparto, ouricuri, rezo-wax, and other known mined and mineral waxes, are also suitable for use herein. Olefinic or diene oligomers and low molecular weight polymers may also be used herein. The oligomers may be polypropylenes, polybutylenes, hydrogenated isoprenes, hydrogenated butadienes, or the like having a weight average molecular weight between about 350 and about 8000.

In one embodiment, a phase change solvent can be incorporated into the elastomeric composition to lower its melt viscosity, rendering the composition processable at a temperature of 175° C. or lower, without substantially compromising the elastic and mechanical properties of the composition. Typically, the phase change solvent exhibits a phase change at temperatures ranging from about 40° C. to about 250° C. The phase change solvent has the general formula:

$$R'-L_y-(Q-L_x)_{n-1}-Q-L_y-R; \qquad (I)$$

$$R'-L_y-(Q-L_x)_n-R; \qquad (II)$$

$$R'-(Q-L_x)_n-R; \qquad (III)$$

$$R'-(Q-L_x)_{n-1}-Q-L_y-R; \qquad (IV)$$

$$R'-(Q-L_x)_{n-1}-Q-R; \text{ or} \qquad (V)$$

a mixture thereof;

wherein Q may be a substituted or unsubstituted difunctional aromatic moiety; L is $CH_2$; R and R' are the same or different and are independently selected from H, CH3, COOH, $CONHR_1$; $CONR_1R_2$, $NHR_3$, $NR_3R_4$, hydroxy, or C1-C30 alkoxy; wherein $R_1$, $R_2$, $R_3$ and $R_4$ are the same or different and are independently selected from H or linear or branched alkyl from C1-C30; x is an integer from 1 to 30; y is an integer from 1 to 30; and n is an integer from 1 to 7. Detailed disclosure of the phase change solvents can be found in Provisional U.S. Patent Application Ser. No. 60/400,282, filed on Jul. 31, 2002.

In certain embodiments, Q is a para-ring substituted difunctional aromatic moiety, wherein the substitutions are in the 1,4 positions. In certain embodiments, n is an integer from 3 to 7. In certain embodiments, the thermoplastic elastomer and the phase change solvent have a weight ratio of from about 10:1 to about 1:1.

The Q moieties in a phase change solvent may include terephthalic, naphthalic, phenolic, phenyl or biphenyl having the following formula:

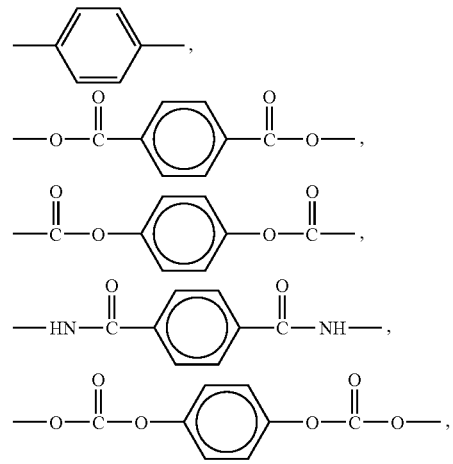

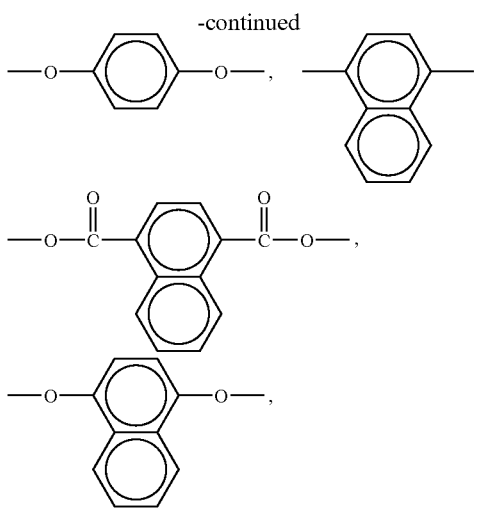

and the like, and mixtures thereof;

Q may be substituted on the aromatic ring with one or more substituents selected from H, C1-C30 alkyl, COOH, $CONHR_5$, $CONR_5R_6$, $NHR_7$, $NR_7R_8$, hydroxyl, C1-C30 alkoxy, $SO_3H$ or halogen; wherein $R_5$, $R_6$, $R_7$ and $R_8$ are the same or different and are independently selected from H or linear or branched alkyl from C1-C30.

Alternatively, the elastomeric composition may also comprise low molecular weight elastomers and/or elastomeric precursors of the above thermoplastic elastomers, and optionally crosslinkers, or combinations thereof. The weight average molecular weight of the low molecular weight elastomers or elastomeric precursors is between about 45,000 and about 150,000.

Suitable elastomeric compositions for use herein are elastic without further treatment and they do not include any volatile solvents whose boiling point is below 150° C. However, after the elastomeric composition has been deposited onto the substrate, it may be subjected to post-treatments to improve or enhance its elasticity and other properties including strength, modulus, and the like. Typically, post-treatments include drying, crosslinking, curing or polymerizing via chemical, thermal, radiation means, and combinations thereof.

The resulting elastomeric members have the following properties: (1) an elasticity (i.e., normalized load at 75% strain) of at least about 50 N/m, preferably from about 50 N/m to about 300 N/m, more preferably from about 75 N/m to about 250 N/m, and most preferably from 100 N/m to about 200 N/m; (2) a percent set of less than about 20%, preferably less than about 15% and more preferably less than about 10%; and (3) a stress relaxation value of less than about 30%, preferably less than about 25%, and more preferably less than about 20%.

The elastomeric members may be applied to a specific region to achieve a total add-on level of from about 5 to about 200 g/m², preferably from about 20 to about 150 g/m², and more preferably from about 50 to about 100 g/m². The first and the second elasticized regions may have open areas not covered by elastomeric members ranging from about 10% to about 80% of the total surface area of the region, preferably from about 20% to about 70%, and more preferably from about 40% to about 60%. The selective depositing of elastomeric compositions uses less of the materials than the amount would be required by the conventional lamination technology using films or sheets. The fibrous substrate in combination with the selective deposition of elastomeric members can provide the resulting composite with lower basis weight and higher breathability than a laminate containing a fibrous web layer and a film or sheet layer. The fibrous substrate can further provide a soft, cloth-like feel to the skin for better wearer comfort.

Each elasticized region may have a different number of elastomeric members disposed per unit area. The add-on level per elastomeric member also differs from region to region. Thus, when comparing a first elasticized region having first elastomeric members disposed thereon and a second elasticized region having second elastomeric members disposed thereon, the ratio of the add-on level on the basis of individual first and second elastomeric member, may range from about 1.05 to about 3, preferably from about 1.2 to about 2.5, and more preferably from about 1.5 to about 2.2. Further, the first and the second elastomeric members may have an elasticity ratio of from about 1.1 to about 10, preferably from about 1.2 to about 5, and more preferably from about 1.5 to about 3.

The elastomeric members may be applied directly to the fibrous web, or indirectly transferred to the fibrous web by first deposited onto an intermediate surface. Suitable methods may include contact methods such as gravure printing, intaglio printing, flexographic printing, slot coating, curtain coating, and the like; and non-contact methods such as ink jet printing, spraying, and the like. Each application method operates in a specific viscosity range, thus, a careful selection of the viscosity of the elastomeric elastomeric composition is required. Composition, temperature and/or concentration can be varies to provide the suitable viscosity for a given processing method and operating conditions.

Temperature may be raised to lower the viscosity of the elastomeric composition. However, high temperature may have adverse effect on the stability of the fibrous substrate, which may experience partial or local thermal degradation where the heated elastomeric composition is deposited. A balance between these two effects is desirable. Alternatively, indirect/transfer methods may be used. The elastomeric composition is heated to achieve a suitable viscosity for processing and applied to an intermediate surface (e.g., a carrier substrate) having good thermal stability, which is then transferred to the fibrous substrate to form the composite preform. The indirect/transfer method allows for a wider range of operating temperatures because the heated elastomeric composition is at least partially cooled when it contacts the fibrous substrate. Thus, the indirect process may be useful for substrates that are thermally sensitive or unstable, such as nonwoven webs, or substrates of low melting polymers, including polyethylene and polypropylene. Nip pressure may be applied with nip rolls or calendar rolls to get sufficient penetration and bonding.

The non-contacting methods provide both mechanical and thermal advantages. Since the application equipment is not in direct contact with the substrate, there is less insult/abrasion to the structural integrity of the substrate. Thus, fibrous webs having lower basis weight, or lower mechanical strength can be used as the substrate. The non-contact methods are especially desirable for high speed processes where direct contact between the equipment and the substrate can apply substantial shear and abrasive forces on the substrate, possibly causing damages to the surface and/or the structure of the substrate. The non-contact methods also allow substrates with lower thermal stability to be used since the fluid elastomeric compositions may be partially air-cooled before coming into contact with the substrate. Moreover, non-contact ink jet printing process provide an additional advantage of total flexiblility in the printed shape, pattern, etc. of the elastomeric members without stopping the process and/or retooling the printing head. Nip pressure may also be applied, if necessary, in the non-contact process.

It is desirable to have the elastomeric composition at least partial penetrates the substrate so that the resulting composite preform does not delaminate in the subsequent processing or manufacturing steps or in the finished product. Additionally, such good bonding within the composite and/or its preform render the use of adhesives optional. The degree of penetration may be affected by several factors: the viscosity of the elastomeric composition when in contact with the substrate, the porosity of the substrate, the surface tension between the substrate and the elastomeric composition. In one embodiment, the off-set gravure printing process allows partial cooling of the elastomeric composition before it contacts the fibrous substrate, thus increases its viscosity and decreases the degree of penetration into the substrate. Alternatively, the elastomeric composition may be cooled by blowing chilled air/gas onto to it prior to or while coming into contact with the substrate. In another embodiment, the degree of penetration may be enhanced by passing the substrate/elastomeric composition through a pair of nip rolls. The temperature of the nip rolls as well as the applied nip pressure provide further control of the degree of penetration.

In another embodiment, the gravure printing method is used, whereby it is possible to vary the amount of elastomeric composition deposited in different portions of the substrate, thereby varying the local stretch properties. For Example, by incorporating different depth and/or width of grooves and lands on the gravure roll, the resulting elastomeric members can be thicker in one area and thinner in another area. In another example, by changing the pattern on the gravure roll, the resulting elastomeric members can have varying the member density in the resulting composite. Furthermore, two or more gravure rolls, with different elastomeric compositions in each, can also be used to deposit these elastomeric compositions in different portions of the element. Gravure printing process includes direct and indirect (or off-set) methods. The direct gravure printing process deposits the elastomeric composition directly onto the substrate. The indirect or off-set gravure printing process first deposits the elastomeric composition onto an offset roll or a carrier surface and then transfers it to the substrate. In the indirect process, the elastomeric composition may be partially cooled and even partially solidified when it finally contacts the substrate. Moreover, the off-set gravure printing process provides a wider temperature range for the process, even when a low thermal stability substrate is used.

In some embodiments, the non-contact spraying method is used. The suitable spraying equipment may include multiple nozzles arranged in series or in parallel. Multiple nozzles can be arranged in an array along the machine direction, along the cross machine direction, at an angle with respect to either direction, or combinations thereof. The nozzles may apply the same or different elastomeric compositions and may have same or different sizes of orifice to apply different amounts of the elastomeric compositions to different areas of the substrate. Further, these nozzles may be controlled so that they start and stop independently and at well defined times to give any desired stretch property in any given area. A suitable spraying equipment is UFD Omega, available from ITW Dynatec, Hendersonville, Tenn.

Furthermore, it is also possible to combine different deposition processes, for example gravure printing with spraying, to obtain the desired properties in the resulting stretch composites.

The local stretch property can be varied in different ways. It can be varied discretely in which the property changes in a stepwise manner. An example of such stepwise change would be to apply a high performance elastomer in one portion of an element of the diaper (such as the top part of an ear portion) and a lower performance elastomer in another portion of that element (such as the lower part of the ear portion) where the stretch requirements are less demanding. The stretch property can also be varied continuously, either linearly or non-linearly. The continuous changes in stretch properties may be achieved by a gravure pattern designed in such a way that the cell depth decreases gradually along the circumference of the roll, thus resulting in a printed pattern where the amount of deposited elastomeric composition decreases continuously in the machine direction.

The stretch composite can be manufactured by process 100 of the present invention, one embodiment of which is illustrated schematically in FIG. 1. Process 100 may include a primary operation of making a composite preform which includes the steps of supplying a first substrate; applying an elastomeric material to the first substrate; and optionally joining with a second substrate. Process 100 may optionally include a secondary operation of incrementally stretching the composite preform to provide extensibility to the fibrous substrate.

Figure 4:
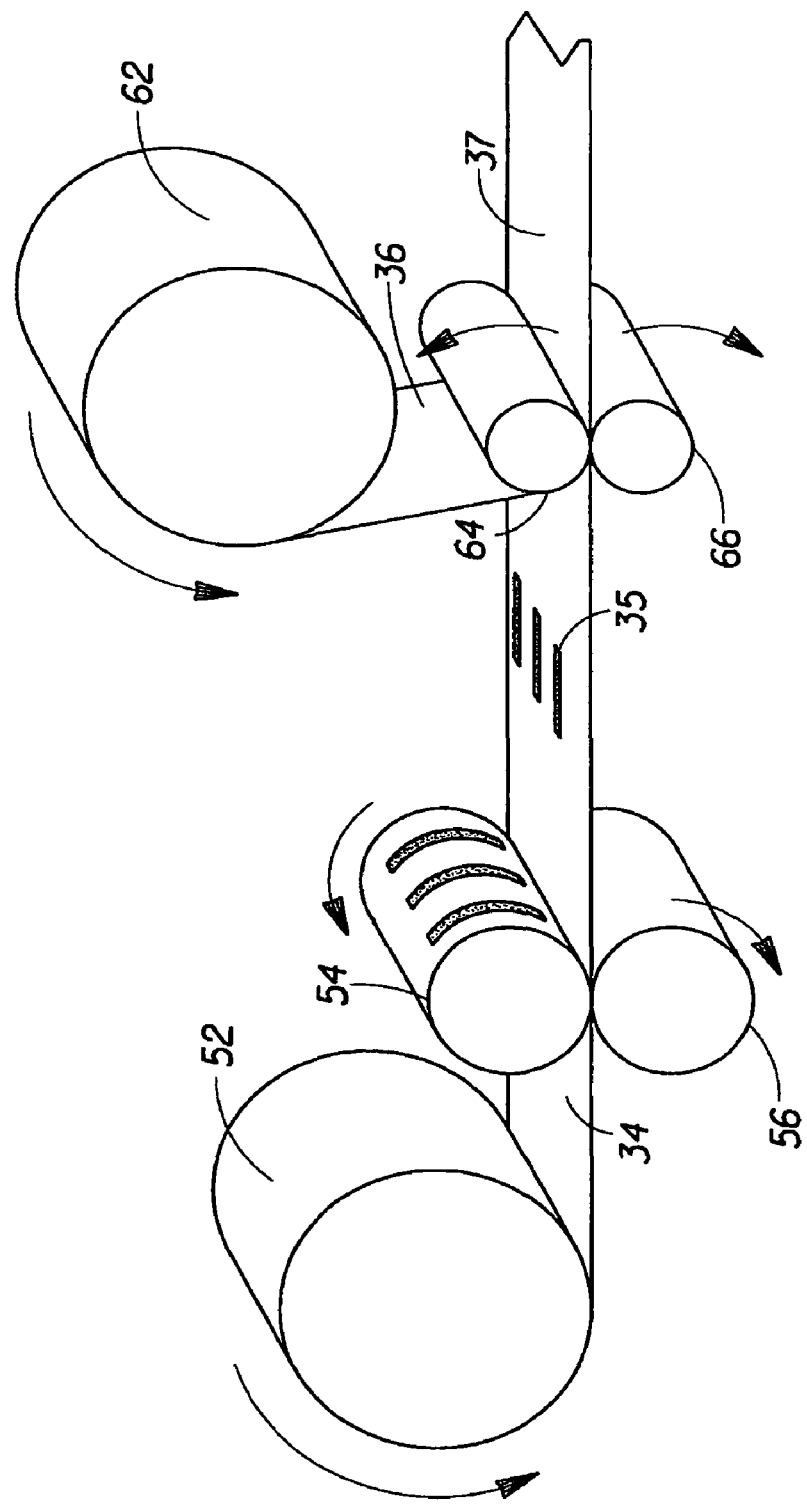
FIG. 4 is an enlarged perspective view of a primary operation of the present invention which includes applying elastomeric members to a substrate and joining with another substrate.

The primary operation of process 100 is shown in details in FIG. 4, the first substrate 34 is provided by a first supply roll 52 and moves through an application device 105, shown here is a rotogravure printing device comprising a gravure printing roll 54 and a back-up roll 56, that deposits the elastomeric composition for elastomeric members onto substrate 34. The elastomeric composition being in a fluid state, may at least partially penetrate substrate 34 to provide a printed substrate 35, resulting in direct bonding between the elastomeric members and the substrate. Optionally, a second substrate 36 may be provided by a second supply roll 62 and combined with the printed substrate 35 via nip rolls 64, 66 to sandwich the elastomeric members between substrates 34, 36 to form a composite preform 37. If necessary, adhesives may be used to bond the elastomeric members and the second substrate. At this point of the process, a zero strain laminate is produced wherein the elastomeric members and the substrates are bonded in an unstrained state.

The printed substrate 35 and/or the composite preform 37 may be subjected to additional treatments such as drying, cooling, consolidating (e.g., passing between a pair of nip rolls), crosslinking, and/or curing (e.g., via chemical, thermal, radiation methods) to enhance the elastic and mechanical properties of the elastomeric composition deposited thereon and of the resulting composite preform.

An optional, secondary operation of process 100 uses forming station 106 to incremental stretch the composite preform 37 to the extent that the substrate is permanently elongated and composite preform 37 is converted into stretch composite 108. Due to this structural change, the substrate has a reduced resistance to stretch and the elastomeric members are able to stretch to the extent provided by the permanent elongation of the substrate.

Alternatively, pre-straining of substrates 34 and/or 36 prior to being used in process 100 may impart extensibility to the substrates and enable the elastomeric members in the stretch composite to stretch to the ultimate elongation of the substrate.

A process sometimes referred to as "ring-rolling," may be a desirable incremental stretching operation of the present invention. In the ring rolling process, corrugated interengaging rolls are used to permanently elongate the fibrous substrate to reduce its resistance to stretch. The resulting composite has a greater degree of stretchability in the portions that have been subjected to the ring rolling process. Thus, this secondary operation provides additional flexibility in achieving stretch properties in localized portions of the stretch composite.

Methods for imparting stretchability to an extensible or otherwise substantially inelastic material by using corrugated interengaging rolls which incrementally stretch in the machine or cross-machine direction and permanently deform the material are disclosed in U.S. Pat. No. 4,116,892, issued on Sep. 26, 1978, to E. C. A. Schwarz; U.S. Pat. No. 4,834,741, issued on May 30, 1989, to R. N. Sabee; U.S. Pat. No. 5,143,679, issued on Sep. 1, 1992 to G. M. Weber et al.; U.S. Pat. No. 5,156,793, issued on Oct. 20, 1992, to K. B. Buell et al.; U.S. Pat. No. 5,167,897, issued on Dec. 1, 1992 to G. M. Webber et al.; and U.S. Pat. No. 5,422,172, issued on Jun. 6, 1995, to P.-C. Wu; and U.S. Pat. No. 5,518,801, issued on May 21, 1996 to C. W. Chappell et al. In some embodiments, the composite preform may be fed into the corrugated interengaging rolls at an angle with respect to the machine direction of this secondary operation. Alternatively, the secondary operation may employ a pair of interengaging grooved plates applied to the composite preform under pressure to achieve incremental stretching of the composite preform in localized portions.

It is desirable that the extensible substrate does not exhibit resistance to stretch when the composite is subjected to a typical strain under the in-use condition. The in-use strains experienced by the composite is due to the stretching when the article is applied to or removed from a wearer and when the article is being worn. The extensible substrate can be pre-strained to impart the desired stretchability to the composite. Typically, when the extensible substrate is pre-strained to about 1.5 time of the maximum in-use strain (typically less than about 250% strain), the extensible substrate becomes permanently elongated such that it does not exhibit resistance to stretch within the range of in-use strain and the elastic properties of the composite is substantially the same as the total properties of the elastomeric members in the composite.

The stretch composite may have an directional elasticity in at least one direction of less than about 400 N/m, preferably from about 5 N/m to about 400 N/m, more preferably from about 25 N/m to about 300 N/m, and most preferably from about 75 N/m to about 200 N/m, when measured as load at 75% strain. Additionally, the resulting stretch composite has the following properties: a directional percent set in at least one direction of less than about 20%, preferably less than about 15% and more preferably less than about 10%; and a directional stress relaxation value in at least one direction of less than about 30%, preferably less than about 22%, and more preferably less than about 15%.

Figure 5:
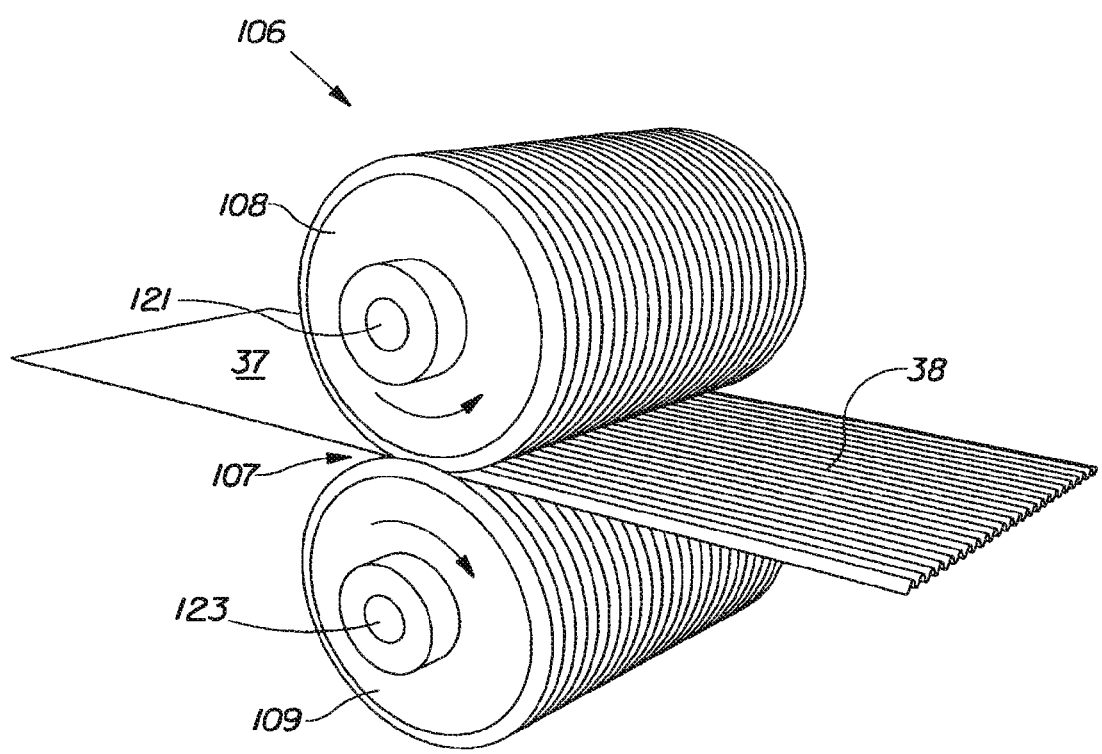
FIG. 5 is an enlarged perspective view of an optional secondary operation of the present invention which uses interengaging forming rolls to incrementally stretching the composite preform.

In one embodiment, as shown in FIG. 1, the ring rolling process is incorporated into process 100 as a secondary operation, which includes a forming station 106 positioned between application device 105 and take-up roll 70. Alternatively, if a second substrate 36 is included, the forming station 106 may be positioned between the second supply roll 62 and the take-up roll 46. Referring to FIG. 5, composite preform 37 is fed to the nip 107 formed by a pair of opposed forming rolls 108 and 109 that together define a forming station 106. Forming station 106 incrementally stretch and permanently elongates the substrate, thereby composite preform 37 is converted into stretch composite 38.

Figure 6:
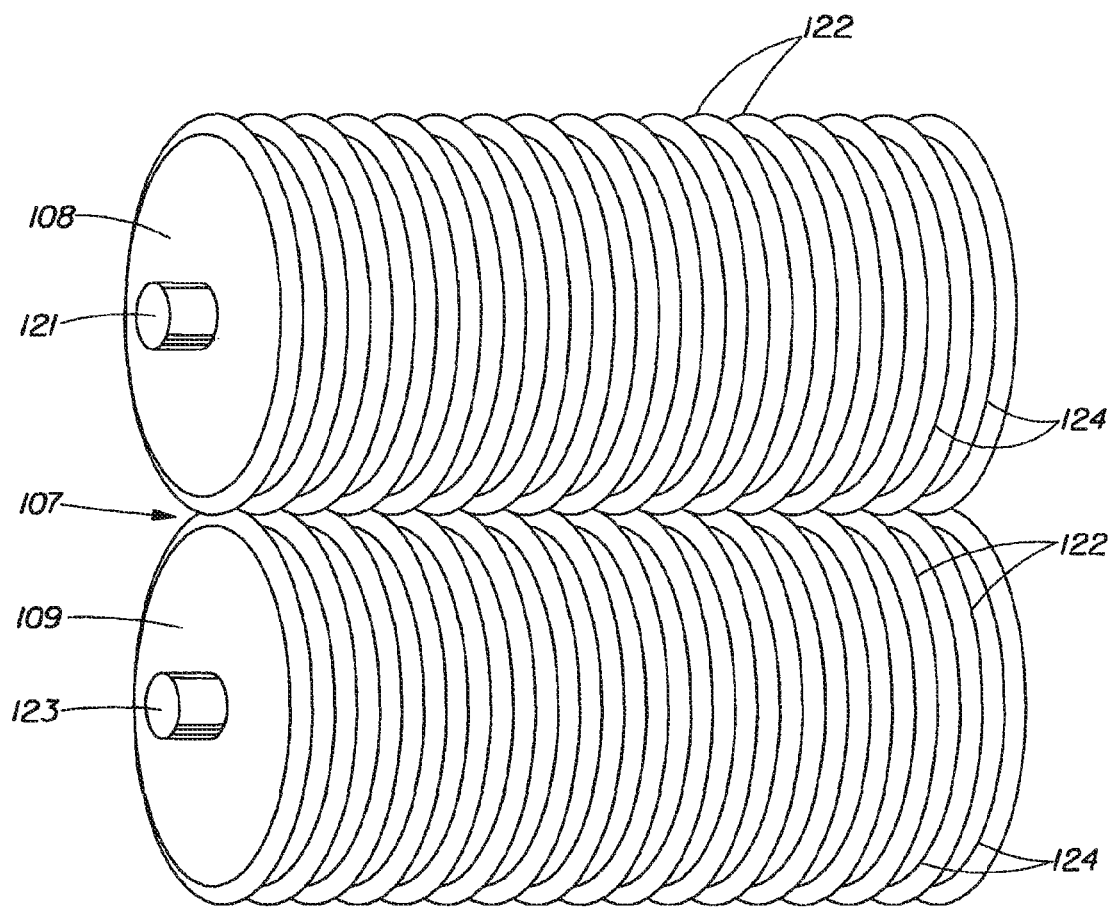
FIG. 6 is an enlarged perspective view of a pair of closely-spaced forming rolls each having alternating and interengaging peripheral teeth and grooves.

Exemplary structures and relative positions of forming rolls 108, 109 are shown in an enlarged perspective view in FIG. 6. As shown, rolls 108 and 109 are carried on respective rotatable shafts 121, 123, having their axes of rotation disposed in parallel relationship. Each of rolls 108 and 109 includes a plurality of axially-spaced, side-by-side, circumferentially-extending, equally-configured teeth 122 that can be in the form of thin fins of substantially rectangular cross section, or they can have a triangular or an inverted V-shape when viewed in cross section. The outermost tips of the teeth are preferably rounded to avoid cuts or tears in the materials that pass between the rolls.

The spaces between adjacent teeth 122 define recessed, circumferentially-extending, equally configured grooves 124. The grooves can be of substantially rectangular cross section when the teeth are of substantially rectangular cross section, and they can be of inverted triangular cross section when the teeth are of triangular cross section. Thus, each of forming rolls 108 and 109 includes a plurality of spaced teeth 122 and alternating grooves 124 between each pair of adjacent teeth. The teeth and the grooves need not each be of the same width, however, and preferably the grooves have a larger width than that of the teeth, to permit the material that passes between the interengaged rolls to be received within the respective grooves and to be locally stretched, as will be explained hereinafter.

Figure 7:
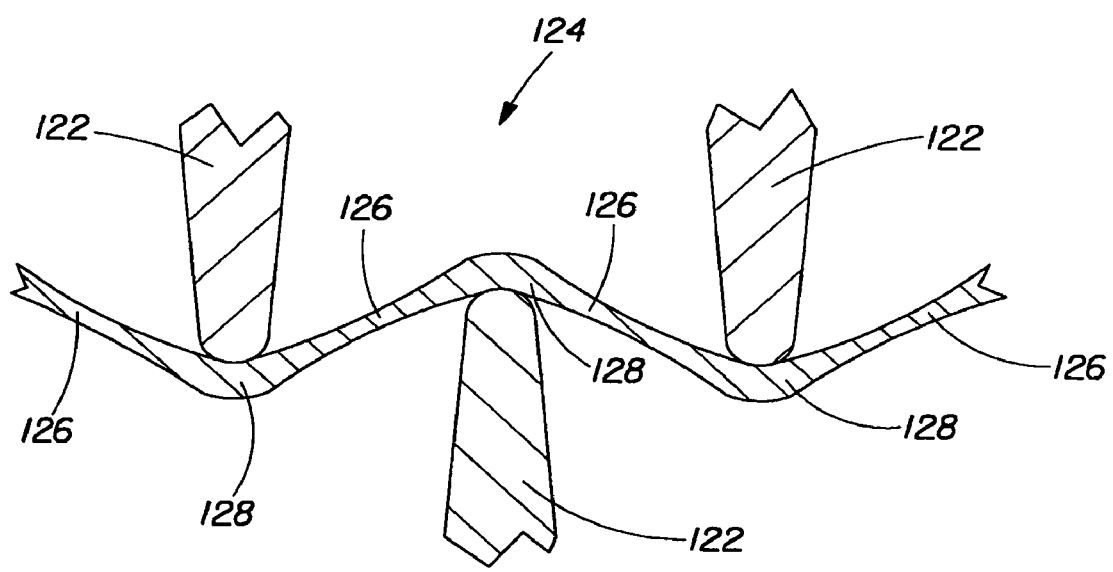
FIG. 7 an enlarged fragmentary cross-sectional view showing the tip portions of the teeth of the interengaging forming rolls with a web material positioned between the rolls and spanning and in contact with the tips of adjacent teeth.

FIG. 7 is an enlarged view of several interengaged teeth 122 and grooves 124 with a composite preform being modified therebetween. As shown, a portion of composite preform 37, is received between the interengaged teeth and grooves of the respective rolls. The interengagement of the teeth and grooves of the rolls causes laterally spaced portions of composite preform 37 to be pressed by teeth 122 into opposed grooves 124. In the course of passing between the forming rolls, the forces of teeth 122 pressing composite preform 37 into opposed grooves 124 impose within composite preform 37 tensile stresses that act in the cross-web direction. The tensile stresses cause intermediate portions 126 that lie between and that span the spaces between the tip portions 128 of adjacent teeth 122 to stretch or extend in a cross-web direction, which results in a localized reduction of the web thickness as well as web tensile strength at each of intermediate portions 126.

The action of pressing of portions of composite preform 37 into the respective grooves 124 by teeth 122 therefore causes a non-uniform reduction of the thickness of composite preform 37 to take place in the cross-web direction of the composite. The thickness of portions tip that are in contact with the tooth tips reduces only slightly, comparing to the thickness reduction of intermediate portions 126 that span adjacent teeth 122. Thus, by passing through the interengaged rolls and being locally laterally stretched at spaced intervals between adjacent teeth, the inelastic elongatable or extensible fibrous web develops alternating high and low basis weight regions. The low basis weight regions are found at the positions of the web wherein the web material has been locally laterally stretched. Additional cross-web stretching of the exiting, formed web can be effected by passing the modified web between so-called Mount Hope rolls, tentering frames, angled idlers, angled nips, and the like, each of which is known to those skilled in the art.

Alternatively, other process embodiments of the present invention can include the use of multiple deposition devices to provide multiple depositions of elastomeric materials onto one or more substrates, including deposition onto two substrates separately and then combing them, and/or making several subsequent depositions onto the same substrate. Further, the use of multiple deposition devices can provide a greater deposition weight of the elastomeric material, a greater z dimension profile variation, capability to deposit different elastomeric materials, and capability to deposit elastomeric materials of different colors, and any combinations thereof.

In one embodiment, the outer cover 40 of a pant type diaper 20 shown in FIG. 2A may include chassis elastomeric members 26 to provide desired breathability of the outer cover 40 while maintaining liquid impermeability of the outer cover 40. Chassis elastomeric members 26 may be disposed on either side of the outer cover 40 in the tummy region, the buttocks region or the crotch region. Multiple chassis elastomeric members 26 may be disposed on the outer cover 40 with various orientations. For example, multiple chassis elastomeric members 26 may be disposed parallel to, perpendicular to, or at an angle to the waist region or the leg openings, and each elastomeric member may have different orientation from neighboring elastomeric members.

Test Methods

Melt Viscosity Test

Melt viscosity of elastomeric compositions which comprise the elastomeric members can be measured using the RDA II Viscometer (manufactured by Rheometrics) or the AR 1000 Viscometer (manufactured by TA Instruments) in the parallel plate mode. Calibration, sample handling and operation of the instrument follow the manufacturer's operating manual generally. Testing conditions used specifically for this test are disclosed herein. In this test, the sample is placed between two parallel plates that are 25 mm in diameter and have a gap of 1.5 mm between them. The sample chamber is heated to and maintained at 175° C. Melt viscosity is measured under the steady state condition at shear rate of 1 $s^{-1}$ and an oscillation of 5% strain.

Hysteresis Test for Elastic Properties (i) Sample Preparation for the Elastomeric Member The properties of the elastomeric members are obtained using test samples made cast films. About 5 grams of the elastomeric composition, which makes up the elastomeric members, is sandwiched between two silicone-coated release films and is heated to about 150 to 200° C. and pressed in a Carver hand press under sufficient pressure for one minute to consolidate the elastomeric composition. Then, the pressure is released and the film is allowed to cool down. Depending on the type of elastomeric composition being cast, temperatures and pressures can be adjusted accordingly. Shims of 0.010" (0.254 mm) thickness are used to obtain uniform film thickness. Test samples of specific sizes for a given test and/or instrument are cut and trimmed from the cast film. For example, samples used herein are 1" by 3" (25.4 mm by 76.2 mm) All surfaces of the sample should be free of visible flaws, holes, scratches or imperfections.

(ii) Sample Preparation for the Composite

Samples of 1" by 3" (25.4 mm by 76.2 mm) size are obtained from the elasticized region of the composite. It is recognized that the stretch composite may exhibit directional properties that are not the same when the composite is measured in different directions, depending on the orientation of the elastomeric members within the sample. Therefore, samples from a given elasticized region are prepared with four different orientations in order to obtain representative directional properties of the composite. Specifically, the samples are obtained from a given elasticized region with its longitudinal axis aligned in a first direction, a second direction which is perpendicular to the first direction, and a third and a forth directions which are +/−45° with respect to the first direction. The first direction may be, but is not required to be, the machine direction (i.e., the substrate movement direction during the process of applying the elastomeric members to the substrate). At least three samples along each orientation are prepared. Where the composite is substantially homogenous to the naked eyes, these directional samples can be taken from neighboring elasticized regions. Where the composite is visibly inhomogenous from one region to another, these directional samples can be taken from the same elasticized region from multiple pieces of the same composite material (e.g., three replicate directional samples may be obtained from the same stretch composite material found on three diapers). Typically, the chosen elasticized region is visually identified as the region having the highest density of elastomeric members. It is typical, though not required, to test more than one elasticized regions to fully characterize the directional properties of the composite. Care should be taken that the three replicate samples are similar to one another. If the elasticized region is not large enough to provide these 1" by 3" (25.4 mm by 76.2 mm) samples, the largest possible sample size is used for testing, and the test method is adjusted accordingly. All surfaces of the sample should be free of visible flaws, scratches or imperfections.

(iii) The Hysteresis Test for the Elastomeric Members

A commercial tensile tester from Instron Engineering Corp., Canton, Mass. or SINTECH-MTS Systems Corporation, Eden Prairie, Minn. may be used for this test. The instrument is interfaced with a computer for controlling the test speed and other test parameters, and for collecting, calculating and reporting the data. The hysteresis is measured under typical laboratory conditions (i.e., room temperature of about 20° C. C and relative humidity of about 50%).

The procedure is as follows:
(1) choose appropriate jaws and load cell for the test; the jaws should be wide enough to fit the sample, typically 1" wide jaws are used; the load cell is chosen so that the tensile response from the sample tested will be between 25% and 75% of the capacity of the load cells or the load range used, typically a 50 lb load cell is used;
(2) calibrate the instrument according to the manufacturer's instructions;
(3) set the gauge length at 1" (25.4 mm);
(4) place the sample in the flat surface of the jaws such that the longitudinal axis of the sample is substantially parallel to the gauge length direction;
(5) set the cross head speed at a constant speed of 10"/min (0.254 m/min) until it reaches 112% strain; then return to the original gauge length at 10"/min (0.254 m/min); and at the end of this pre-straining cycle, start timing the experiment using a stop watch;
(6) reclamp the pre-strained sample to remove any slack and still maintain a 1" (25.4 mm) gauge length;
(7) at the three minute mark on the stop watch, start the hysteresis test and the instrument records load versus strain data simultaneously; the hysteresis test has the following steps:
a) go to 75% strain at a constant rate of 10"/min (0.254 m/min);
b) hold for 2 minutes;
c) return to 0% strain at a constant rate of 10"/min (0.254 m/min);
d) hold for 1 minute; and
e) go to 0.1 N at a constant rate of 2"/min (50.8 mm/min).

From the data collected in step 7(*a*), the elasticity is determined from the load at 75% strain, which is normalized to 85 grams per square meter (gsm) as follows: the load at 200% strain from the plot is divided by the width of the sample, then multiplied by a normalizing factor, which is 85/(½*(actual weight of the sample/(width*gauge length) of sample in $m^2$)), or 85/(½*(actual weight of the sample)/(6.47×10⁻⁴)) if the sample dimension is measured in inches.

From the data collected in step 7(*e*), the % set is determined from the strain at 0.1N, which is a force deemed sufficient to remove the slack but low enough to impart, at most, insubstantial stretch to the sample.

From the data collected in step 7(*b*), the force relaxation is determined by the load at the beginning and at the end of the 2 minutes hold time using the following formula:

$$\% \text{ Force Relaxation at time, } t = \frac{\left[\begin{array}{c}(\text{initial load}) - \\ (\text{load at time, } t)\end{array}\right]}{(\text{initial load})} \times 100$$

For the elastomeric members, the average results from three replicate samples are reported.

(iv) The Hysteresis Test for the Elastomeric Composites

There is no pre-straining of the composite sample in this hysteresis test and the load at 75% strain is normalized to 85 gsm of the composite basis weight. In this test, steps 1-4 are performed as above; at the end of step 4, there is a one minute holding at 0% strain; and steps 7(*a-e*) immediately follow.

The elastic properties are obtained from the recorded data as above, and the load at 75% strain is normalized to 85 gsm basis weight of the composite and is reported as such. For the elastomeric composites, the average results from three replicate samples in each direction are reported as "directional elasticity", "directional % set" and "directional stress relaxation".

EXAMPLES

Example 1

A phase change solvent having the general structure (I) is prepared by combining 260 grams (2 moles) of octanol with 404 grams (2 moles) of terephthaloyl chloride and 202 grams (1 mole) of 1,12-dodecanediol in 1500 ml of chloroform in a reaction flask. The mixture is allowed to react at 55° C. for 20 hours with constant stirring and under a vacuum, which removes HCl generated by the reaction. The reaction is terminated by cooling the mixture to room temperature. The resulting reaction mixture is poured into a large quantity of methanol to precipitate the product. The precipitant is collected over a filter, washed with 500 ml of methanol 3 times and dried at 45° C. in a vacuum oven for 20 hours.

An elastomeric composition is prepared by mixing and stirring this phase change solvent and SEPTON® S4033 (available from Kuraray America, Inc., New York, N.Y.) at 120° C. for 4 hours or until the sample appears to be homogeneous. The mixture is cooled to room temperature. Mineral oil, DRAKEOL® Supreme (available from Pennzoil Co., Penrenco Div., Karns City, Pa.) is then added to the mixture and stirred at room temperature for 16-24 hours to form an elastomeric composition. For this example, the final elastomeric composition contains 40 wt % SEPTON® S4033, 30 wt % crystalline solvent and 30 wt % mineral oil. This elastomeric composition has a melt viscosity of about 24 Pa·s at 175° C. and 1 s⁻¹

The above blending method is merely exemplary. Other conventional blending methods using batch mixers, screw extruders, and the like, can also be used.

Example 2

The elastomeric composition of Example 1 is processed through a direct gravure system (available from Roto-therm Inc., Redding Calif.) at a temperature of about 175° C. The direct gravure system includes a tank, a bath, hoses, a patterned steel roll (i.e., the gravure roll) and a back-up roll. The tank holds the elastomeric composition; the tank is connected to the hoses which serve as the conduits for transporting the elastomeric composition to the bath. All these components are heated to about 175° C. so that the elastomeric composition is maintained at a fairly constant temperature during the printing process. The gravure roll is 9.3" (0.236 m) in diameter and is also heated to about 175° C. The gravure roll has grooves and lands on its surface for depositing the elastomeric composition onto a substrate in a continuous trihelical pattern not shown in FIG. 4. The grooves are 0.020" (0.51 mm) wide and 0.0075" (0.19 mm) deep and the land width is 0.023" (0.58 mm). Total width of the pattern on the gravure roll is 5" (0.127 m). The back-up roll is 6.25" (0.158 m) in diameter and is made of silicone rubber to have a hardness of 55 Shore A. The substrate is a HEC polypropylene nonwoven web (available from BBA Nonwovens Inc. of South Carolina) having a basis weight of about 22 grams per square meter.

Referring to FIG. 4, a substrate 34 is unwound from a first supply roll 52 and is fed between the gravure printing roll 54 and the back-up roll 56, both operating at a line speed of 50-200 feet per minute and provide a nip pressure of 6-12 mm. Nip pressure was quantified in terms of a footprint, which is the impression that the rubber roll makes on the steel cylinder. Footprint can vary from about 3 mm to 24 mm using this equipment. Proper nip pressure is chosen to effectuate the transfer of the composition from the gravure roll to the substrate and to control the penetration of the composition into the substrate. Transfer efficiency, which is the fraction of the cells that are emptied, typically ranged from about 40-60%. The gravure printing roll 54 picks up the elastomeric composition from the heated bath (not shown) and transfer it directly to the substrate to form a printed substrate 35. A second substrate 36, which is the same nonwoven web as the first substrate 34, is unwound from a second supply roll 62 and combined with the printed substrate 35 between two rubber nip rolls 64, 66, thereby forming the composite preform 37. Nip pressure, temperature, and contact time can be adjusted to give optimum bonding.

The composite preform is subjected to incremental stretching in one or more portions by pressing said portions between two interengaging grooved plates, one stationary and the other movable. The plates are at least 4"×4" in dimension and are made of stainless steel. The pitch, which is the distance between adjacent teeth on a plate, is 1.524 mm; the tooth height is 10.31 mm; the tooth tip radius is 0.102 mm; and the depth of engagement (DOE), which is the distance between two adjacent tooth tips from two teeth on opposed, interengaging plates that controls how deeply the teeth are engaged, is 3.639 mm.

The composite preform is placed on the stationary plate; the movable plate approaches and engages with the stationary plate at a speed of 1.82 m/s. Upon reaching the desired DOE, the movable plate reverses and returns to its original position. Thus, by varying the portion and/or the direction the composite preform placed in between the grooved plates and/or by varying the DOE, the resulting composite can have incremental stretching to a varying extent, in any portion thereof and in any orientation.

Example 3

The process is similar to that of Example 2, except an off-set gravure printing process is used. The elastomeric composition is first transferred from the gravure printing roll to a silicone release paper (available from Waytek Corporation, Springboro, Ohio) and then substrate 34 is nipped in between an additional set of rubber rolls to get complete transfer from the release paper to the substrate. Since these rubber rolls are not heated, the elastomeric composition is cooled during this off-set printing step such that it contacts the substrate at a temperature lower than the processing temperature of 175° C. Thus, there is a reduced likelihood of thermal damages to the delicate structure of the nonwoven substrate.

Comparative Examples

Comparative examples are made from blends of SEPTON® S4033, mineral oil, DRAKEOL® Supreme, and VECTOR® 4211 (available from Dexco Chemical Company, Houston, Tex.). The blends can be prepared by the methods described in Example 1 or any conventional blending methods. Comparative example 1 is a blend of 60 wt % VECTOR® 4211 and 40 wt % mineral oil. Comparative example 2 is a blend of 55 wt % VECTOR® 4211 and 45 wt % mineral oil. Comparative example 3 is a blend of 30 wt % SEPTON® S4033 and 70 wt % mineral oil. Comparative example 4 is a blend of 35 wt % SEPTON® S4033 and 65 wt % mineral oil. Comparative example 5 is a blend of 40 wt % SEPTON® S4033 and 60 wt % mineral oil. Comparative example 6 is a hot melt adhesive H2737, available from Bostik Findley, Middletown, Mass. Comparative example 7 is a metallocene-catalyzed polyethylene ENGAGE® ENR 8407, available from Dow Chemical Company of Midland, Mich.

Film samples of the comparative examples and Example 1 of the present invention are prepared and subjected to the hysteresis test described above. The results are reported below.

TABLE 1

| | Basis Weight. (gsm) | Melt Viscosity (175° C., 1 s$^{-1}$) (Pa s) | Normalized * Load at 75% Strain (N/m) | Force Relaxation (75%, 2 min., room temp.) (%) | % set (%) |
|---|---|---|---|---|---|
| Example 1 | 198 | 24 | 99.40 | 19.8 | 3.7 |
| Comparative Examples | | | | | |
| 1 | 158 | 630 | 12.76 | 8.1 | 6.8 |
| 2 | 224 | 484 | 13.75 | 5.4 | 5.0 |
| 3 | 232 | 21 | 14.52 | 8.7 | 6.1 |
| 4 | 225 | 40 | 18.78 | 7.9 | 4.6 |
| 5 | 141 | 203 | 25.15 | 6.8 | 4.6 |
| 6 | 200 | 7 | 14.50 | 7.4 | 5.0 |
| 7 | 175 | 490 | 190.55 | 24.9 | 6.8 |

* Normalized to a basis weight of 85 grams per square meter.

TABLE 1 shows that most comparative examples do not have the desired melt viscosity suitable for the controlled deposition processes used herein to produce the stretch composites. Further, for those comparative examples that have a suitably low melt viscosity, they exhibit a substantial trade-off in properties, resulting in unsatisfactory elastic properties. Example 1 of the present invention uniquely provides the desired melt viscosity suitable for the processes used herein without compromising the elastic properties.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a stretch composite comprising the steps of:
    a. providing at least one inelastic substrate;
    b. applying a tensioning force to the inelastic substrate to form a necked, inelastic substrate;
    c. providing an application device, said device including at least one patterned print roll; and
    d. printing at least two differing elastomeric members by means of said patterned print roll, onto said substrate to form a stretch composite, said elastomeric members differing in a property selected from the group consisting of differing width dimensions between said elastomeric members, differing mechanical properties between said elastomeric members, differing elastomeric compositions between said elastomeric members and differing visual appearance between said elastomeric members, and wherein said elastomeric members comprise a thermoplastic elastomer and a phase change solvent having the general formula:

R'-L$_y$-(Q-L$_x$)$_{n-1}$-Q-L$_y$-R;  (I)

R'-L$_y$-(Q-L$_x$)$_n$-R;  (II)

R'-(Q-L$_x$)$_n$-R;  (III)

R'-(Q-L$_x$)$_{n-1}$-Q-L$_y$-R;  (IV)

R'-(Q-L$_x$)$_{n-1}$-Q-R; or  (V)

a mixture thereof;
    wherein Q is a para-ring substituted difunctional aromatic moiety, and wherein the substitutions are in the 1,4 positions; L is CH$_2$; R and R' are the same or different and are independently selected from H, CH3, COOH, CONHR$_1$, CONR$_1$R$_2$, NHR$_3$, NR$_3$R$_4$, hydroxy, or C1-C30 alkoxy; wherein R$_1$, R$_2$, R$_3$ and R$_4$ are the same or different and are independently selected from H or linear or branched alkyl from C1-C30; x is an integer from 1 to 30; y is an integer from 1 to 30; and n is an integer from 3 to 7; wherein the phase change solvent has a phase change in a temperature range from 40° C. to about 250° C.

2. The process of claim 1, further comprising a step of bonding a second inelastic substrate to the stretch composite.

3. The process of claim 1, wherein the inelastic substrate is incrementally stretched, at least in one or more portions, prior to applying a tensioning force.

4. The process of claim 1, wherein said elastomeric members have a melt viscosity of from about 1 to about 150 Pa·s, measured at 175° C. and 1 s$^{-1}$ shear rate.

5. The process of claim 1, wherein said elastomeric members are selected from the group consisting of rectilinear stripes, curvilinear stripes, triangles, trapezoids, squares, parallelograms, polygons, ellipses, circles and combinations thereof.

6. The process of claim 5, wherein said elastomeric members are spaced apart with respect to each other.

7. The process of claim 1, wherein the stretch composite comprises one or more elasticized regions of an absorbent article.

8. The process of claim 7, wherein the one or more elasticized regions of the absorbent article is selected from the group consisting of an elasticized waist region, an elasticized cuff region, an elasticized side panel, an elastic ear portion, an elasticized outercover, an elasticized topsheet, a fastener system, and combinations thereof.

9. The process of claim 1, wherein said thermoplastic elastomer and said phase change solvent have a weight ratio of from about 10:1 to about 1:1.

10. The process of claim 1, wherein said elastomeric members have a width dimension of at least about 2.0 mm.

11. The process of claim 4, wherein said elastomeric members have a melt viscosity of from about 5 to about 100 Pa·s.

12. The process of claim 11, wherein said elastomeric members have a melt viscosity of from about 10 to about 80 Pa·s.

* * * * *